(12) United States Patent
Zhang et al.

(10) Patent No.: US 11,761,037 B1
(45) Date of Patent: Sep. 19, 2023

(54) PROBE AND METHOD OF ENRICHING TARGET REGION APPLICABLE TO HIGH-THROUGHPUT SEQUENCING USING THE SAME

(71) Applicant: AMOY DIAGNOSTICS CO., LTD., Fujian (CN)

(72) Inventors: Linhua Zhang, Fujian (CN); Xuchao Li, Fujian (CN); Huijuan Ge, Fujian (CN); Baolei Jin, Fujian (CN); Ning Chen, Fujian (CN); Li Ruan, Fujian (CN); Limou Zheng, Fujian (CN)

(73) Assignee: AMOY DIAGNOSTICS CO., LTD., Fujian (CN)

( * ) Notice: Subject to any disclaimer, the term of this patent is extended or adjusted under 35 U.S.C. 154(b) by 583 days.

(21) Appl. No.: 16/650,320

(22) PCT Filed: Jul. 18, 2018

(86) PCT No.: PCT/CN2018/096078
§ 371 (c)(1),
(2) Date: Mar. 24, 2020

(87) PCT Pub. No.: WO2019/062289
PCT Pub. Date: Apr. 4, 2019

(30) Foreign Application Priority Data

Sep. 30, 2017 (CN) .......................... 201710918635.3

(51) Int. Cl.
*C12Q 1/6874* (2018.01)
*C12N 15/10* (2006.01)
*C12N 15/11* (2006.01)

(52) U.S. Cl.
CPC ....... *C12Q 1/6874* (2013.01); *C12N 15/1093* (2013.01); *C12N 15/11* (2013.01); *C12N 2310/315* (2013.01); *C12N 2310/33* (2013.01)

(58) Field of Classification Search
None
See application file for complete search history.

(56) References Cited

U.S. PATENT DOCUMENTS

2015/0004600 A1    1/2015   Wang et al.

FOREIGN PATENT DOCUMENTS

| CN | 101067156 A | 11/2007 |
| CN | 105714383 A | 6/2016 |

(Continued)

OTHER PUBLICATIONS

Niedzicka et al., "Molecular Inversion Probes for targeted resequencing in non-model organisms," Sci. Rep. 2016, 6:24051, published Apr. 5, 2016, with 6 pages of Supplementary Information. (Year: 2016).*

(Continued)

*Primary Examiner* — Kaijiang Zhang
(74) *Attorney, Agent, or Firm* — Muncy, Geissler, Olds & Lowe, P.C.

(57) ABSTRACT

The present invention discloses a probe applicable to high-throughput sequencing and a method of enriching a target region using the probe. The probe includes, in an order from a 5' end, a ligation arm, a masking sequence 1, a UID sequence 1, an Illumina Tag1 sequence, a dU region, an Illumina Tag2 sequence, a UID sequence 2, a masking sequence 2 and an extension arm; wherein the masking sequence 1, the masking sequence 2, the dU region, the UID sequence 1, and the UID sequence 2 may be 0 bp. When sequencing is performed by using a library built by the probe of the present invention, it is not necessary to add a sequencing primer additionally, and adopting the method of the present invention may directly use an RNA as a template (Continued)

to capture a target region, so as to simplify the experiment procedure.

16 Claims, 1 Drawing Sheet

Specification includes a Sequence Listing.

(56) References Cited

FOREIGN PATENT DOCUMENTS

| CN | 106574286 A | 4/2017 |
|----|-------------|--------|
| WO | WO 2016/112073 A1 | 7/2016 |
| WO | WO 2017/020024 A1 | 2/2017 |

OTHER PUBLICATIONS

Hardenbol et al., "Multiplexed genotyping with sequence-tagged molecular inversion probes," Nat. Biotechnol. 2003, 21:673-678. (Year: 2003).*

Skerra, "Phosphorothioate primers improve the amplification of DNA sequences by DNA polymerases with proofreading activity," Nucleic acids Res. 1992, 20:3551-3554. (Year: 1992).*

Niedzicka, M. et al. "Molecular Inversion Probes for targeted resequencing in non-model organisms." Scientific Reports, vol. No. 6, Article No. 24051, Apr. 5, 2016, pp. 1-9 (XP-055560091).

* cited by examiner

PROBE AND METHOD OF ENRICHING TARGET REGION APPLICABLE TO HIGH-THROUGHPUT SEQUENCING USING THE SAME

TECHNICAL FIELD

The present invention relates to a biotechnology sequencing field, especially relates to a probe and a method of enriching a target region applicable to high-throughput sequencing using the same.

BACKGROUND ART

With the rapid development of high-throughput sequencing technology, the sequencing efficiency has been significantly improved, the time has been significantly reduced, costs have been significantly reduced, and gene detection means have undergone revolutionary changes. Its technology is developing in a large-scale and industrialized direction. Although the overall cost of the high-throughput sequencing has fallen dramatically, the cost of high-depth whole genome sequencing and the complexity of interpreting large-scale sequencing data are difficult for researchers. The emergence of target sequence targeted sequencing technology alleviates the above difficulties to a certain extent. The target sequence targeted sequencing is a research strategy for enriching and sequencing gene regions of interest. The main advantages of target region sequencing lie in being able to perform sequencing for specific regions, effectively reducing sequencing costs, improving sequencing depths, and being able to more economically and efficiently study genetic variation information in the specific regions.

At present, there are mainly three methods to achieve enriching the target region: hybrid capture technology, multiplex PCR technology, and Molecular Inversion Probe (MIP) technology. The hybrid capture technology: firstly fragmenting genome DNAs by using a physical method or an enzyme digesting method, ligating connectors at both ends, to perform PCR amplification. Then, (the fragmented DNAs) are hybridized with a probe marked with a biotin, and the DNA without hybridization cannot be captured by magnetic beads and washed away. Finally, the PCR amplification and sequencing are performed for the enriched DNA specimens. The characteristics of hybrid capture are having good scalability and able to capture exomes or even larger target regions, but the disadvantages are that the operation procedure is complex, the cycle is longer, the cost is higher, and more special equipments are required.

The multiplex PCR amplification technology designs specific primers according to a target sequence, and enriches the target sequence through multiplex amplification. The multiplex PCR technology is easy to operate, flexible to apply, inexpensive, simple to analyze, and minimizes instrument requirements, and is able to complete enriching the target sequence and library building within hours. Using an ultra-high sequencing depth and amplicon sequencing can detect ultra-low frequency mutations in complex specimens, and is particularly suitable for clinical research in cancer and other diseases. The disadvantages are that it is only suitable for capturing relatively small target sequences, and it needs to solve the problems of amplification inhibition, primer cross-amplification, serious primer dimer, etc.

The molecular inversion probe technology is a new type of multi-targeted sequencing method. This method has advantages of simple operation procedures, small specimen requirements, low costs, high accuracy, etc. However, the application of molecular inverted probes in the field of high-throughput sequencing is immature, and has disadvantages of long hybridization time, high error rates, and complicated operation steps, etc.

SUMMARY

The purpose of the present invention is to provide a simple, fast, efficient, and accurate method of enriching a target region by using an improved molecular inversion probe technology.

In order to achieve the above purpose, the present invention provides a probe, which is characterized in including, in an order from a 5' end, a ligation arm, a masking sequence 1, a UID sequence 1, an Illumina Tag1 sequence, an Illumina Tag2 sequence, a masking sequence 2 and an extension arm; wherein the UID sequence 1 consists of 3 to 12 random bases; the masking sequence 1 is 0 to 3 random bases which are not complementary with sequences on an upstream of a template corresponding to the ligation arm; and the masking sequence 2 is 0 to 3 random bases which are not complementary with sequences on a downstream of the template corresponding to the ligation arm.

Another aspect of the present invention also provides a probe, which is characterized in including, in an order from a 5' end, a ligation arm, a masking sequence 1, an Illumina Tag1 sequence, an Illumina Tag2 sequence, a UID sequence 2, a masking sequence 2 and an extension arm, wherein the UID sequence 2 is composed of 3 to 12 random bases; the masking sequence 1 is 0 to 3 random bases which are not complementary with sequences on an upstream of a template corresponding to the ligation arm; and the masking sequence 2 is 0 to 3 random bases which are not complementary with sequences on a downstream of the template corresponding to the ligation arm.

Another aspect of the present invention also provides a probe, which is characterized in comprising, in an order from a 5' end, a ligation arm, a masking sequence 1, a UID sequence 1, an Illumina Tag1 sequence, an Illumina Tag2 sequence, a UID sequence 2, a masking sequence 2 and an extension arm; wherein the UID sequence 1 and the UID sequence 2 both consist of 3 to 12 random bases; the masking sequence 1 is 0 to 3 random bases which are not complementary with sequences on an upstream of a template corresponding to the ligation arm; and the masking sequence 2 is 0 to 3 random bases which are not complementary with sequences on a downstream of the template corresponding to the ligation arm.

Another aspect of the present invention also provides a probe, and on the basis of the above probe, between the Illumina Tag1 sequence and the Illumina Tag2 sequence, there is further a dU region, which is composed of 1 to 3 deoxyuridine bases.

Further, the ligation arm is a base sequence of 15-45 bp and complementarily bonded with the nucleic acid template; the Illumina Tag1 sequence and the Illumina Tag2 sequence are sequences or any combination of complementary or reverse complementary sequences thereof on transposon Adapters and connectors in any library building kit of an Illumina platform; and the extension arm is a base sequence of 15-45 bp and complementarily bonded with the nucleic acid template.

Further, a modification is performed for the extension arm; preferably, a phosphorothioate modification is performed; more preferably, a Tm value of the ligation arm is higher than the Tm value by more than 2° C. of the extension arm;

alternatively, a phosphorylation modification is performed for the 5' end of the ligation arm; and alternatively, the Illumina Tag1 sequence and the Illumina Tag2 sequence are selected from sequences or any combination of complementary or reverse complementary sequences thereof on transposon Adapters and connectors in any library building kit of an Illumina platform.

Another aspect of the present invention also provides a method of enriching a target region applicable to high-throughput sequencing, which is characterized in using the probe.

Further, the steps are:

hybridizing, extending and ligating reaction: a template DNA is hybridized with the probe, extended and ligated to obtain a first product;

obtaining of a second product: enzyme digesting the remaining probe and template DNA, and performing a PCR amplification through a tag primer, to obtain the second product;

purifying: purifying the second product to obtain a library; and just on-line sequencing the library.

Further, the hybridizing, extending and ligating reaction steps are: firstly hybridizing the template DNA with the probe, and then adding polymerase and ligase to perform extending and ligating to obtain the first product;

preferably, the reaction system and reaction procedure are:

Purified water 6 μL;
50 ng/μL template DNA 2 μL;
$3 \times 10^{-3}$ μM of the probe 1 μL;
10×Ampligase Buffer 1 μL.

The procedure is: denaturing at 95° C. for 5 min, and incubating at 60° C. for 2 h; then adding the following reagents to the above system to perform extending and ligating reactions, and the reaction procedure is: incubating at 60° C. for 1 h;

Purified water 1.4 μL;
1 mM dNTPs 1 μL;
5 U/L Ampligase DNA ligase 1 μL;
10×Ampligase Buffer 0.5 μL;
50 mM NAD$^+$ 0.1 μL;
Phusion® High-Fidelity DNA Polymerase 1 μL;

or when the template is RNA,

Nuclease-free water 5.5 μL;
50 ng/μL template RNA 2 μL;
$3 \times 10^{-3}$ μM of the probe 1 μL;
RNase Inhibitor 0.5 μL;
10×Ampligase Buffer 1 μL;

denaturing at 70° C. for 2 min, and incubating at 65° C. for 2 h; then adding the following reagents, reacting at 42° C. for 1 h, and performing extending and ligating reaction;

1 mM dNTPs 1 μL;
5 U/μL Ampligase DNA ligase 1 μL;
10×Ampligase Buffer 1 μL;
50 mM NAD$^+$ 0.1 μL;
5×First-Strand Buffer 4 μL;
100 mM DTT 2 μL;
SMART MMLV RT 1 μL;

or adding the template DNA, the probe, and polymerase and ligase simultaneously, and performing hybridizing, extending and ligating simultaneously to obtain the first product; preferably, the reaction system and reaction procedure are:

Purified water 3.4 μL;
50 ng/μL template DNA 2 μL;
$3 \times 10^{-3}$ μM of the probe 1 μL;

1 mM dNTPs 1 μL;
5 U/L Ampligase DNA ligase 1 μL;
10×Ampligase Buffer 1 μL;
50 mM NAD$^+$ 0.1 μL;
Phusion® HiFi DNA Polymerase 0.5 μL;

The reaction procedure is: at 95° C. for 5 min and at 60° C. for 3 h.

Further, the obtaining of the second product is: firstly digesting the remaining probe and template DNA using an exonuclease, then linearizing the first product using a USER enzyme, and then performing a PCR amplification through a tag primer, to obtain the second product; preferably, the reaction system and procedure are:

The first product
Exonuclease I 0.5 μL;
Exonuclease III 0.5 μL.

incubating at 37° C. for 40 min, and incubating at 95° C. for 5 min;

and then adding the following reagents:

2×iProof HF Master Mix 50 μL;
Purified water 29 μL;
20 μM tag upstream primer 2 μL;
20 μM tag downstream primer 2 μL;
USER enzyme 1 μL;

incubating at 37° C. for 15 min, and pre-denaturing at 98° C. for 30 s; denaturing at 98° C. for 10 s, annealing at 58° C. for 30 s, extending at 72° C. for 30 s, and 26 cycles; extending at 72° C. for 2 min, and heat preserving at 4° C.;

or adding the exonuclease, the tag upstream primer, and the tag downstream primer simultaneously, and performing enzyme digesting, linearizing and PCR amplification simultaneously to obtain the second product;

the tag upstream primer and the tag downstream primer have a phosphorothioate modification at a 3' end and a thio, amino or spacer arm modification at the 5' end to prevent from being enzyme digested by the exonuclease;

preferably, when the template is the DNA, the reaction system and procedure are:

The first product 18 μL;
Exonuclease Lambda 0.5 μL;
Exonuclease III 1 μL;
2×iProof HF Master Mix 50 μL;
H$_2$O 29.5 μL;
20 μM tag upstream primer 2 μL;
20 μM tag downstream primer 2 μL;

the procedure is: incubating at 37° C. for 40 min, incubating at 95° C. for 5 min, and pre-denaturing at 98° C. for 30 s; denaturing at 98° C. for 10 s, annealing at 58° C. for 30 s, extending at 72° C. for 30 s, and 26 cycles; extending at 72° C. for 2 min, and heat preserving at 4° C.;

or, when the template is the RNA, the reaction system and procedure are:

The first product 10.1 μL;
Exonuclease I 1 μL;
RNase A 0.1 μL;
RNase H 0.1 μL;
2×iProof HF Master Mix 50 μL;
H$_2$O 24.8 μL;
20 μM tag upstream primer 2 μL;
20 μM tag downstream primer 2 μL;

incubating at 37° C. for 60 min, incubating at 95° C. for 5 min, and pre-denaturing at 98° C. for 30 s; denaturing at 98° C. for 10 s, annealing at 60° C. for 30 s, extending at 72° C. for 30 s, and 27 cycles; extending at 72° C. for 2 min, and heat preserving at 4° C.

Further, a structure of the upstream primer of the tag primers, starting from the 5' end, is a sequence region for cluster generation and an index sequence region for Illumina sequencing; and a full-length sequence region inversely complementary paired with an Illumina Tag1 sequence;

and a structure of the downstream primer of the tag primers, starting from the 5' end, is a sequence region for cluster generation and an index sequence region for Illumina sequencing; and an Illumina Tag2 full-length sequence region.

The implementation procedure thereof specifically includes the following parts:

1. Hybridization Between a Probe and a Nucleic Acid Specimen

Figure 1:
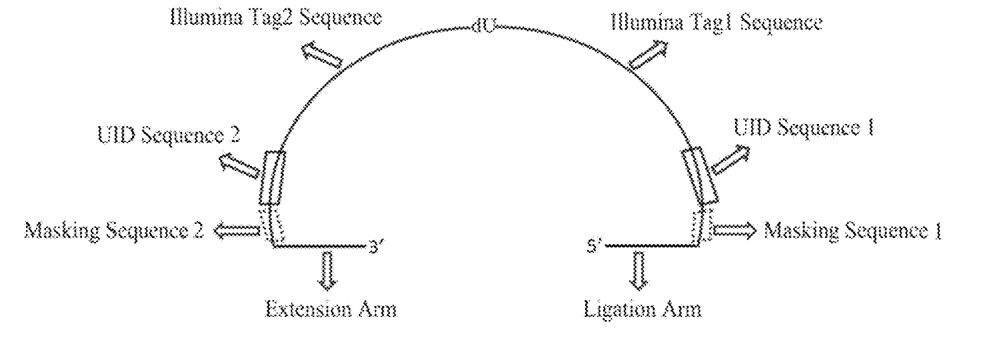
The sole FIGURE is a diagram of one of probe structures in the present invention.

The hybridization between the probe and the nucleic acid specimen means that the extension arm and the ligation arm of the probe have complementary paired sequences with the target region of a single-stranded nucleic acid specimen, and they are hybridized under an appropriate hybridization system and temperature. The nucleic acid specimen can be DNA, RNA or cDNA obtained by reverse transcription of RNA, and can also be DNA and cDNA or a mixture of DNA and RNA. One of the improved MIP probe structures is depicted in the sole FIGURE. The source of the probe can be a variety of synthetic methods, and can also be modified through molecular biological means after synthesis. The probe is composed of eight parts of structures: 1) a variable length ligation arm (15-45 nt) complementarily bonded with the nucleic acid template; 2) 0 to 3 random bases which are not complementary with sequences on an upstream of a template corresponding to the ligation arm, to perform a masking function; 3) 1 to 2 UID (Unique Identifier) sequences, wherein the UID sequence is composed of 3 to 12 random bases, to distinguish tag sequences of the initial template; 4) Tag sequence 1 for sequencing by an Illumina sequencing platform (Tag1, a reverse complement sequence 5'-CTGTCTCTTATACACATCTCCGAGCCCACGAGAC-3' (SEQ ID NO: 15) of a sequence of Nextera Transposase Adapters Read 2 in Illumina Nextera Library Prep Kits), that is, the sequence can be reduced by 0 to 16 bases from the 3' end; 5) 0 to 3 deoxyuridine bases; 6) Tag sequence 2 for sequencing by the Illumina sequencing platform (Tag2, a sequence 5'-ACACTCTTTCCCTACACGACGCTCTTCC-GATCT-3' (SEQ ID NO: 16) of a 5 end connector in Illumina TruSeq kits), that is, the sequence can be reduced by 0 to 19 bases from the 5' end; wherein the two tag sequences, that is, Tag sequences 1 and 2, for sequencing, can be sequences on transposon Adapters and connectors in any library building kit of the Illumina platform or any combination of complementary sequences thereof. 7) 1 to 3 random bases complementary with sequences on a downstream of a template that does not correspond to the extension arm, to perform a masking function; and 8) a variable length extension arm (15-45 nt) being complementarily bonded with the nucleic acid template. The phosphorothioate modification or other modifications can be performed for the extension arm; when the probe is synthesized, a phosphorylation modification is performed for the 5' end of the ligation arm, it is also able to select not performing the phosphorylation modification when synthesizing (the probe), and the phosphorylation modification is performed for the 5' end of the probe through a phosphorylation reaction).

2. Extending and Ligase Ligating Reaction

After both the extension arm and the ligation arm of the probe are anchored to the target region, a polymerizing function of the DNA polymerase is used to extend from the 3' end of the extension arm to the 5' end of the ligation arm. A high-fidelity DNA polymerase is preferred. When the template is RNA, reverse transcriptase is used for extension.

Then, a nick is ligated using the ligase to obtain a circular product. Of course, the hybridizing, extending, and ligating reaction can also be performed simultaneously in one step.

3. Exonuclease Digesting Linear Probe and Nucleic Acid

In order to eliminate the effects of nucleic acid specimens and remaining probes on subsequent PCR amplification, single-stranded exonuclease and double-stranded exonuclease are used to digest probes and single-stranded and double-stranded nucleic acid specimens, and only circular products are left. The exonuclease may be a single enzyme or a mixture of multiple enzymes.

4. Linearizing and PCR Amplifying Circular Products

In order to improve the efficiency of PCR amplification, the circular product is cut to be in a linear shape using the USER enzyme, and then the library amplification is performed for the upstream and downstream primers containing the same or complementary structure as the sequencing tag sequences in the probe structure (CAAGCAGAAGACGG-CATACGAGAT TTCTGCCTGTCTCGTGGGCTCGGAGATGTGTAT AAGAGACAG (SEQ ID NO:9 for which the phosphorothioate modification is not performed) and AATGATACGGCGACCACCGAGATCTACAC TATAGCCTACACTCTTTCCCTACACG ACGCTCTTCCGATCT (SEQ ID NO:10 for which the phosphorothioate modification is not performed). The underlined part is an index sequence, which is used to distinguish the tags of different libraries when sequencing the mixed library, and the sequence can be changed.

Of course, it is also able to mix the exonuclease and PCR reagents (excluding USER enzymes), firstly the enzyme digesting reaction is performed, and then the library amplification is performed by using the phosphorothioate modified upstream and downstream primers.

5. Library Purification

In order to remove impurities such as enzymes, deoxyribonucleoside triphosphates (dNTPs), ions, primers, primer dimers or the like from the library, the library is purified by using Agencourt AMPure XP magnetic beads of the Beckman company, and may also be purified by using other methods such as gel recovery after electrophoresis or column purification, etc.

6. High-Throughput Sequencing

The prepared library is sequenced on a high-throughput sequencer after the concentration and fragment quality control are qualified. The library sequencing method of the present invention includes, but is not limited to, a reversible end termination sequencing method, and may also be other sequencing platforms. The sequencing type can be single-ended or double-ended. In an embodiment of the present invention, the sequencing platform is Illumina, and the sequencing type is a double-end sequencing.

Compared with the current conventional MIP method, the advantageous effects of the present invention mainly include:

1. The present invention uses sequences on the Illumina Nextera and Illumina TruSeq adapters as backbone sequences of the probe, and it is not necessary to add a sequencing primer additionally during sequencing, thereby simplifying the experiment procedure.

2. The present invention modifies the PCR tag primer, and can add the enzyme digesting reagent and the PCR reagent to the reaction tube simultaneously, thereby reducing the operation steps.

3. The present invention can directly capture the target region by using RNA as a template, and does not need to perform reverse transcription firstly, thereby simplifying the experiment procedure.

4. By introducing the UID structure, the present invention can remove the repeated sequence obtained by the PCR amplification, obviously reduce the error rate, and restore the true mutation frequency of the specimen. The dU base is introduced into the probe structure, and the circular template is linearized by the USER enzyme to improve the efficiency of PCR amplification and reduce PCR amplification errors.

DETAILED DESCRIPTION OF THE EMBODIMENTS

Embodiments of the present invention will be described in details below, and examples of the embodiments are shown in the drawings, wherein the same or similar reference signs indicate the same or similar components or components having the same or similar functions from beginning to end. The embodiments described by referring to the drawings below are exemplary, and aim at explaining the present invention, but cannot be understood as limitations to the present invention. The embodiments in which specific techniques or conditions are not noted, are performed according to the techniques or conditions described in the documents within the prior art or according to the product instructions. The used reagents or instruments that are not marked with manufacturers are all conventional products that can be obtained through market shopping.

The following primers and probes are synthesized by Biotech Bioengineering (Shanghai) Co., Ltd.

HCT15 cells used in this embodiment can be purchased from biological companies such as Puno Biotech, Shanghai Yanyu Biological Engineering Co., Ltd., etc., and then the DNA just can be extracted according to a conventional DNA extraction method.

The NCI-H3122 cell line can be purchased from companies such as Shanghai Zeye Biotechnology Co., Ltd. and Shanghai Jihe Biotechnology Co., Ltd., etc., and then the RNA just can be extracted according to a conventional RNA extraction method.

The probe structure in the embodiment is understood and described below with reference to the probe structure in the sole FIGURE.

Embodiment 1: Enriching the Target Region with an Improved MIP Probe Library

In the embodiment, four probes targeting the human breast cancer susceptibility gene (BRCA) are used. The experiment is divided into two groups. Group 1 has probes without dU structure, and Group 2 has probes with dU structure, and the other structure and sequence both are the same.

Notes: B denotes it can be G, T or C; D denotes it can be G, A or T; H denotes it can be A, T or C; V denotes it can be G, A or C; N denotes it can be A, T, C or G; 5Phos denotes the phosphorylation modification; and -s- denotes performing the phosphorothioate modification between two bases.

The probe sequences of Group 1 are as follows:
P01:

SEQ ID NO: 1
/5Phos/GGGCCGCTTCATTTTGTAAGACTTATNNNNNNNNNNNN

CTGTCTCTTATACACATCTCCGAGCCCACGAGAC

ACACTCTTTCCCTACACGACGCTCTTCCGATCT

TGTCTGCTCCACTTC wherein, starting from the 5' end, the underlined part is the ligation arm, NNNNNNNNNNNN is the UID sequence 1, the double underlined part is the Illumina Tag1, the part of which the underline is the dotted line is the Illumina Tag2, and the wavy underlined part is the extension arm.

P02:

SEQ ID NO: 2
/5Phos/CTCTTTATACTCTTAAAAATTACTGAGGACCTAAAAGAGCAT

TTGVVCTGTCTCTTATACACATCTCCGAACGACGCTCTTCCGATCT

NNNNNNNNNNNNAAATGAATTTGACAGGATAATAGAAAATC wherein, starting from the 5' end, the underlined part is the ligation arm, VV is the masking sequence 1, the double underlined part is the Illumina Tag1, the part of which the underline is the dotted line is the Illumina Tag2, NNNNNNNNNNNN is the UID sequence 2, and the wavy underlined part is the extension arm.

P03:

SEQ ID NO: 3
/5Phos/TGCATTCTTCAAAGCVBDNNNCTGTCTCTTATACACATC

CGCTCTTCCGATCTNNNBDBGAGGTACCTGAATCAGCA;

wherein, starting from the 5' end, the underlined part is the ligation arm, VBD is the masking sequence 1, NNN is the UID sequence 1, the double underlined part is the Illumina Tag1, the part of which the underline is the dotted line is the Illumina Tag2, NNN is the UID sequence 2, BDB is the masking sequence 2, and the wavy underlined part is the extension arm.

P04:

SEQ ID NO: 4
/5Phos/CAGTGTTTAGAATCAGGTCACTCBNNNNNCTGTCTCTTATAC

ACATCTCCGACGCTCTTCCGATCTNNNNNHCCCAGTTTGAAGCAAATG wherein, starting from the 5' end, the underlined part is the ligation arm, B is the masking sequence 1, NNNNN is the UID sequence 1, the double underlined part is the Illumina Tag1, the part of which the underline is the dotted line is the Illumina Tag2, NNNNN is the UID sequence 2, H is the masking sequence 2, and the wavy underlined part is the extension arm.

The probe sequences of Group 2 are as follows:
P05:

SEQ ID NO: 4
/5Phos/GGGCCGCTTCATTTTGTAAGACTTATNNNNNNNNNNNNNCTGT

CTCTTATACACATCTCCGAGCCCACGAGACdUdUdU

ACACTCTTTCCCTACACGACGCTCTTCCGATCTT GTCTGCTCCACTTC wherein, starting from the 5' end, the underlined part is the ligation arm, NNNNNNNNNNNN is the UID sequence 1, the double underlined part is the Illumina Tag1, dU is the deoxyuridine, the part of which the underline is the dotted line is the Illumina Tag2, and the wavy underlined part is the extension arm.
P06:

SEQ ID NO: 6
/5Phos/CTCTTTATACTCTTAAAAATTACTGAGGACCTAAAAGAGCAT

TTGVVCTGTCTCTTATACACATCTCCGAdUACGACGCTCTTCCGATCT

NNNNNNNNNNNN AAATGAATTTGACAGGATAATAGAAAATC wherein, starting from the 5' end, the underlined part is the ligation arm, VV is the masking sequence 1, the double underlined part is the Illumina Tag1, dU is the deoxyuridine, the part of which the underline is the dotted line is the Illumina Tag2, NNNNNNNNNNNN is the UID sequence 2, and the wavy underlined part is the extension arm.
P07:

SEQ ID NO: 7
/5Phos/TGCATTCTTCAAAGCVBDNNNCTGTCTCTTATACACATCdU

GACGCTCTTCCGATCT NNNBDBGAGGTACCTGAATCAGCA ;

wherein, starting from the 5' end, the underlined part is the ligation arm, VBD is the masking sequence 1, NNN is the UID sequence 1, the double underlined part is the Illumina Tag1, dU is the deoxyuridine, the part of which the underline is the dotted line is the Illumina Tag2, NNN is the UID sequence 2, BDB is the masking sequence 2, and the wavy underlined part is the extension arm.
P08:

SEQ ID NO: 8
/5Phos/CAGTGTTTAGAATCAGGTCACTCBNNNNNCTGTCTCTTATAC

ACATCTCCdUACGCTCTTCCGATCT NNNNNDBH

CCCAGTTTGAAGCAAATG .

wherein, starting from the 5' end, the underlined part is the ligation arm, B is the masking sequence 1, NNNNN is the UID sequence 1, the double underlined part is the Illumina Tag1, dU is the deoxyuridine, the part of which the underline is the dotted line is the Illumina Tag2, NNNNN is the UID sequence 2, DBH is the masking sequence 2, and the wavy underlined part is the extension arm.

The hybridization reaction system is as follows:
Purified water 6 µL;
50 ng/µL HCT15 cell DNA 2 µL;
$3 \times 10^{-3}$ µM P01-04 or P05-08 probe equally mixed mixture 1 µL;
10×Ampligase Buffer (Epicentre) 1 µL.
The procedure is: denaturing at 95° C. for 5 min, and incubating at 60° C. for 2 h. Then, the following reagents are added to the above hybridization products to perform extending and ligating reaction, and The reaction procedure is: incubating at 60° C. for 1 h.
Purified water 1.4 µL;
1 mM dNTPs (NEB) 1 µL;
5 U/L Ampligase DNA ligase (Epicentre) 1 µL;
10×Ampligase Buffer (Epicentre) 0.5 µL;
50 mM NAD$^+$(NEB) 0.1 µL;
Phusion® High-Fidelity DNA Polymerase(NEB) 1 µL.

The remaining probes and DNA are digested by using the exonuclease. The following reagents are again added to the above products:
Exonuclease I (NEB) 0.5 µL;
Exonuclease III(NEB) 0.5 µL.
Incubating at 37° C. for 40 min, and incubating at 95° C. for 5 min.

In order to cut the circular product containing the dU structure group into linear single strands, the USER enzyme is added to the PCR reaction. That is, the following reagents are again added to the above product:
2×iProof HF Master Mix(Bio-Rad) 50 µL;
Purified water 29 µL;
20 µM Tag1 primer 2 µL;
20 µM Tag2 primer 2 µL;
USER enzyme 1 µL.
Tag1 primer sequence:

SEQ ID NO: 9
5'CAAGCAGAAGACGGCATACGAGATTTCTGCCT

GTCTCGTGGGCTCGGAGATGT GTATAAGAGACA-s-G3' ,

Tag2 primer sequence:

SEQ ID NO: 10
5'AATGATACGGCGACCACCGAGATCTACACTATAGCCT

ACACTCTTTCCCTACAC GACGCTCTTCCGATC-s-T3' .

wherein the sequence underlined by the wavy line is a sequence on the connector of the 5 end of the Illumina TruSeq kit, and Illumina Tag2 in the probe structure of the present invention is that this sequence is reduced by 0 to 19 bases from the 5' end. The double underlined part is a sequence used for cluster generation during Illumina sequencing and cannot be changed. The underlined parts are all index sequences, and the sequences can be changed. The part of which the underline is a dotted line is a sequence of Illumina Nextera Transposase Adapters Read 2 and is inversely complementary paired with the Illumina Tag1 in the probe structure of the present invention.

Tag primer sequences are used for the PCR amplification of circular products. When the Tag1 and 2 sequences are replaced with sequences on transposon Adapters and connectors in the library building kit of the Illumina or other combinations, the sequences on the underlined and wavy dotted lines need to be changed accordingly.

Incubating at 37° C. for 15 min, and pre-denaturing at 98° C. for 30 s; denaturing at 98° C. for 10 s, annealing at 58° C. for 30 s, extending at 72° C. for 30 s, and 26 cycles; extending at 72° C. for 2 min, and heat preserving at 4° C.

After amplification, the library is purified by using the Agencourt AMPure XP magnetic beads. Then, the quality control is performed for the library, and the library is sequenced on the Illumina sequencer.

TABLE 1

Result table of library building library production and template recovery rate by using the probes containing the dU structure and not containing the dU structure

| Experiment group | Library production (ng) | Template recovery rate |
| --- | --- | --- |
| Group 1 (the group without containing the dU structure) | 62.3 | 22.6% |
| Group 2 (the group containing the dU structure) | 224.6 | 23.1% |

It can be seen from Table 1 that although the probe containing the dU structure has a slightly different template recovery rate compared with the probe without containing the dU structure, it can obviously improve the library production.

Embodiment 2: Enriching the Target Region with an MIP Probe Library that Optimizes the Melting Temperature (Tm) Value of the Ligation Arm and the Extension Arm The probe sequences are as follows:
P09:
on the basis of P5, performing the phosphorothioate modification among the finally three bases from the 3' end thereof.
P10:
on the basis of P6, performing the phosphorothioate modification among the finally three bases from the 3' end thereof.
P11:
on the basis of P7, performing the phosphorothioate modification among the finally three bases from the 3' end thereof.
P12:
on the basis of P8, performing the phosphorothioate modification among the finally three bases from the 3' end thereof.

The PCR primer sequence is the same as that in Embodiment 1, that is, the Tag1 primer sequence is the same as the Tag1 primer sequence in Embodiment 1; and the Tag2 primer sequence here is the same as the Tag2 primer sequence in Embodiment 1.

In this embodiment, the Tm value of the ligation arm is higher than the extension arm by more than 2° C. during the design of the probe, and the phosphorothioate modification is performed for the extension arm. The experiment is divided into two groups, a control group uses P05-P08 probes, and an optimized group uses optimized P09-P12 probes, and the specific steps are as follows:
1. Hybridizing, extending and ligating reactions, please refer to Table 2

TABLE 2

| Reaction system table | |
| --- | --- |
| Reagent | Volume (μL) |
| Purified water | 3.4 |
| 50 ng/μL HCT15 cell DNA | 2 |
| 3 × 10⁻³ μM P05-08 or P09-12 probe equally mixed mixture | 1 |
| 1 mM dNTPs (NEB) | 1 |
| 5 U/μL Ampligase DNA ligase (Epicentre) | 1 |
| 10× Ampligase Buffer (Epicentre) | 1 |

TABLE 2-continued

| Reaction system table | |
| --- | --- |
| Reagent | Volume (μL) |
| 50 mM NAD⁺(NEB) | 0.1 |
| Phusion ® HiFi DNA Polymerase (NEB) | 0.5 |

The reaction procedure is: at 95° C. for 5 min, and at 60° C. for 3 h.

2. Adding the following reagents again to the above system to perform enzyme digesting reaction, wherein The reaction procedure is: incubating at 37° C. for 40 min, and incubating at 95° C. for 5 min.
Exonuclease I (NEB) 0.5 μL;
Exonuclease III(NEB) 0.5 μL;
Exonuclease Lambda(NEB) 0.5 μL;
3. Adding the following reagents to the above system to perform product linearization and PCR amplification.
2×iProof HF Master Mix(Bio-Rad) 50 μL;
Purified water 34 μL;
20 μM Tag1 primer 2 μL;
20 μM Tag2 primer 2 μL;
USER enzyme 1 μL.

The Tag1 primer sequence here is the same as the Tag1 primer sequence in Embodiment 1; and the Tag2 primer sequence here is the same as the Tag2 primer sequence in Embodiment 1.

The reaction procedure is: incubating at 37° C. for 15 min, and pre-denaturing at 98° C. for 30 s; denaturing at 98° C. for 10 s, annealing at 58° C. for 30 s, extending at 72° C. for 30 s, and 26 cycles; extending at 72° C. for 2 min, and heat preserving at 4° C.

4. After amplification, the library is purified by using the Agencourt AMPure XP magnetic beads. Then, the quality control is performed for the library, and the library is sequenced on the Illumina sequencer. The analysis result refers to Table 3.

TABLE 3

| Experiment result table | | |
| --- | --- | --- |
| Experiment group | Library production (ng) | Template recovery rate |
| Control group (without containing the phosphorothioate modification) | 22.5 | 3.4% |
| Optimized group (containing the phosphorothioate modification) | 158.2 | 18.7% |

It can be seen from Table 3 that the library production and the template recovery rate of the optimized group are obviously higher than those of the control group by using the method of this embodiment.

Embodiment 3: Enriching the Target Region with an MIP Solution of which the Procedure is Improved In this embodiment, the optimized procedure is adding the enzyme digesting reagent and the PCR reagent to the reaction tube simultaneously. The hybridization reaction system is as follows:

Purified water 6 μL;

50 ng/μL HCT15 cell DNA 2 μL;

3×10$^{-3}$ μM P05-08 probe equally mixed mixture 1 μL;

10×Ampligase Buffer (Epicentre) 1 μL.

The procedure is: denaturing at 95° C. for 5 min, and incubating at 60° C. for 2 h. Then, the following reagents are added to the above hybridization products again to perform extending and ligating reaction, and The reaction procedure is incubating at 60° C. for 1 h.

Purified water 1.4 μL;

1 mM dNTPs (NEB) 1 μL;

5 U/μL Ampligase DNA ligase (Epicentre) 1 μL;

10×Ampligase Buffer (Epicentre) 0.5 μL;

50 mM NAD$^+$(NEB) 0.1 μL;

Phusion® High-Fidelity DNA Polymerase(NEB) 1 μL.

The remaining probes and DNA are digested by using the exonuclease, and then the PCR amplification is performed for them. The following reagents are added to the above products.

The reaction procedure is: incubating at 37° C. for 40 min, incubating at 95° C. for 5 min, and pre-denaturing at 95° C. for 30 s; denaturing at 98° C. for 10 s, annealing at 58° C. for 30 s, extending at 72° C. for 30 s, and 26 cycles; extending at 72° C. for 2 min, and heat preserving at 4° C.

Exonuclease Lambda 0.5 μL;

Exonuclease III 1 μL;

2×iProof HF Master Mix(Bio-Rad) 50 μL;

H$_2$O 29.5 μL;

20 μM Tag3 primer 2 μL;

20 μM Tag4 primer 2 μL.

Tag3 primer sequence:

SEQ ID NO: 11

5'-s-AAGCAGAAGACGGCATACGAGATTTCTGCCT

GTCTCGTGGGCTCGGAGATGTGTATAAGAGACA-s-G3',

Tag4 primer sequence:

SEQ ID NO: 12

5'-A-s-ATGATACGGCGACCACCGAGATCTACACTATAGCCT

ACACTCTTTCCCTACACGACGCTCTTCCGATC-s-T3'.

wherein the phosphorothioate modification is performed for the Tag3 primer sequence from the 5' end on the basis of the Tag1 primer sequence, and the phosphorothioate modification is performed for the Tag4 primer sequence from the 5' end on the basis of the Tag2 primer sequence.

After amplification, the library is purified by using the Agencourt AMPure XP magnetic beads. Then, the quality control is performed for the library, and the library is sequenced on the Illumina sequencer. The library production is 58.5 ng, and the template recovery rate is 22.4%. It can be seen that a mixed solution of the enzyme digesting reagent and the PCR reagent is feasible, thereby simplifying the operation procedure.

Embodiment 4: Performing the Target Region Enrichment for the RNA Template with the MIP Solution of which the Procedure is Improved The probe sequences of this embodiment are:

P13:

SEQ ID NO: 13

/5Phos/AGCTCCATCTGCATGGCTTGHVDNNNNNCTGTCTCTTATAC

ACATCTCCdUGACGCTCTTCCGATCTNNNNNHHH

AGGTGTGGGCTCTACAGTAGTTTTGCTCCATATAA GCATGACTCC wherein, starting from the 5' end, the underlined part is the ligation arm, HVD is the masking sequence 1, NNNNN is the UID sequence 1, the double underlined part is the Illumina Tag1, dU is the deoxyuridine, the part of which the underline is the dotted line is the Illumina Tag2, NNNNN is the UID sequence 2, HHH is the masking sequence 2, and the wavy underlined part is the extension arm.

P14:

SEQ ID NO: 14

/5Phos/AGCTCCATCTGCATGGCTTGHVDNNNNNCTGTCTCTTATACA

CATCTCCdU GACGCTCTTCCGATCT NNNNN BBB

CGCGAGTTGACATTTTTGCTTGG wherein, starting from the 5' end, the underlined part is the ligation arm, HVD is the masking sequence 1, NNNNN is the UID sequence 1, the double underlined part is the Illumina Tag1, dU is the deoxyuridine, the part of which the underline is the dotted line is the Illumina Tag2, NNNNN is the UID sequence 2, BBB is the masking sequence 2, and the wavy underlined part is the extension arm.

In this embodiment, two probes targeting the human EML4-ALK (-echinodermal microtubule-binding protein-like 4-anaplastic lymphoma kinase) fusion gene are used. The hybridization reaction condition is as follows:

Nuclease-free water (NEB) 5.5 μL;

50 ng/μL H3122 cell DNA 2 μL;

3×10$^{-3}$ μM P13-14 probe equally mixed mixture 1 μL;

RNase Inhibitor(TaKaRa) 0.5 μL;

10×Ampligase Buffer (Epicentre) 1 μL.

The procedure is: denaturing at 70° C. for 2 min, and incubating at 65° C. for 2 h. Then, the following reagents are added to the above hybridization products, and the reaction procedure is: at 42° C. for 1 h, and performing extending and ligating reaction.

1 mM dNTPs (NEB) 1 μL;

5 U/μL Ampligase DNA ligase (Epicentre) 1 μL;

10×Ampligase Buffer (Epicentre) 1 μL;

50 mM NAD$^+$(NEB) 0.1 μL;

5×First-Strand Buffer(TaKaRa) 4 μL;

100 mM DTT(TaKaRa) 2 μL;

SMART MMLV RT(TaKaRa) 1 μL.

The remaining probes, RNA and RNA on the DNA-RNA hybrid strand are digested by using the exonuclease and ribonuclease, and then the PCR amplification is performed for them.

The following reagents are added to the above products. The reaction procedure is: incubating at 37° C. for 60 min, incubating at 95° C. for 5 min, and pre-denaturing at 95° C. for 30 s; denaturing at 98° C. for 10 s, annealing at 60° C. for 30 s, extending at 72° C. for 30 s, and 26 cycles; extending at 72° C. for 2 min, and heat preserving at 4° C.

Exonuclease I 1 μL;

RNase A 0.1 μL;

RNase H 0.1 μL;

2×iProof HF Master Mix(Bio-Rad) 50 μL;

H$_2$O 24.8 μL;

20 μM Tag1 primer 2 μL;

20 μM Tag2 primer 2 μL.

The Tag1 primer sequence here is the same as the Tag1 primer sequence in Embodiment 1; and the Tag2 primer sequence here is the same as the Tag2 primer sequence in Embodiment 1.

After amplification, the library is purified by using the Agencourt AMPure XP magnetic beads. Then, the quality control is performed for the library, and the library is sequenced on the Illumina sequencer. The result refers to Table 4.

TABLE 4

Experiment result table of Embodiment 4

| Experiment group | Comparison rate | Coverage |
|---|---|---|
| 1 | 96.24% | 100% |
| 2 | 95.87% | 100% |
| 3 | 96.16% | 100% |

Experiment groups 1-3 are three repeated groups. It can be seen from Table 4 that the library sequencing results have a comparison rate of more than 95% and a coverage of 100%, indicating that using the MIP solution of which the procedure is improved can directly use the RNA as a template for enriching the target region.

The above embodiments are only used for explaining rather than limiting the technical solution of the present invention. Although detailed explanations are taken on the present invention with reference to better embodiments, those skilled in the art should understand that modifications or equivalent replacements may be made on the technical solution without departing from the purpose and scope of the technical solution of the present invention, and they all should be covered in scopes of the claims of the present invention.

The invention claimed is:

1. A probe, comprising, in an order from a 5' end, a ligation arm, a masking sequence 1, a UID (Unique Identifier) sequence 1, an Illumina Tag1 sequence, an Illumina Tag2 sequence, a UID sequence 2, a masking sequence 2 and an extension arm, wherein the UID sequence 1 and the UID sequence 2 both consist of 3 to 12 random bases; the masking sequence 1 is 0 to 3 random bases which are not complementary with sequences on an upstream of a template corresponding to the ligation arm; and the masking sequence 2 is 0 to 3 random bases which are not complementary with sequences on a downstream of the template corresponding to the ligation arm; and wherein the Illumina Tag1 sequence is 5'-CTGTCTCT-TATACACATCTCCGAGCCCACGAGAC-3' (SEQ ID NO: 15) sequentially reduced by 0-16 bases from the 3' end, and the Illumina Tag2 sequence is 5'-ACACTCTTTCCCTACACGACGCTCTTCC-GATCT-3' (SEQ ID NO: 16) sequentially reduced by 0-19 bases from the 5' end.

2. The probe of claim 1, wherein, between the Illumina Tag1 sequence and the Illumina Tag2 sequence, there is further a dU region, which is 1 to 3 deoxyuridine bases.

3. The probe of claim 1, wherein the ligation arm is a base sequence of 15-45 bp and complementarily bonded with a nucleic acid template; and the extension arm is a base sequence of 15-45 bp and complementarily bonded with the nucleic acid template.

4. The probe of claim 1, wherein the extension arm is a modified extension arm.

5. The probe of claim 4, wherein the extension arm is a phosphonothioate-modified extension arm.

6. The probe of claim 5, wherein a Tm value of the ligation arm is more than 2° C. higher than the Tm value of the extension arm.

7. The probe of claim 1, wherein the ligation arm includes a phosphorylation modified 5' end.

8. The probe of claim 1, wherein the Illumina Tag1 sequence and the Illumina Tag2 sequence are selected from sequences or combination of complementary or reverse complementary sequences thereof on transposon Adapters and connectors in a library building kit of an Illumina platform.

9. A method of enriching a target region applicable to high-throughput sequencing, comprising:

hybridizing, extending and ligating reaction: the probe of claim 1 is hybridized to a template DNA or RNA, extended and ligated to obtain a first product;

obtaining of a second product: enzyme digesting the remaining probe and template DNA, and performing a PCR amplification through a tag primer, to obtain the second product;

purifying: purifying the second product to obtain a library; and just on-line sequencing the library.

10. The method of claim 9, wherein the hybridizing, extending and ligating reaction steps are: firstly hybridizing the template DNA or RNA with the probe, and then adding polymerase and ligase to perform extending and ligating to obtain the first product; or adding the template DNA, the probe, polymerase and ligase simultaneously, and performing hybridizing, extending and ligating simultaneously to obtain the first product.

11. The method of claim 10, wherein when it is firstly hybridizing the template DNA or RNA with the probe, and then adding polymerase and ligase to perform extending and ligating to obtain the first product, the reaction system and reaction procedure of the hybridizing, extending and ligating reaction are:

Purified water 6 μL;
50 ng/μL template DNA 2 μL;
$3 \times 10^{-3}$ μM of the probe 1 μL;
10×Ampligase Buffer 1 μL;
The procedure is: denaturing at 95° C. for 5 min, and incubating at 60° C. for 2 h; then adding the following reagents to the above system to perform extending and ligating reactions, and the reaction procedure is: incubating at 60° C. for 1 h;
Purified water 1.4 μL;
1 mM dNTPs 1 μL;
5 U/μL Ampligase DNA ligase 1 μL;
10×Ampligase Buffer 0.5 μL;
50 mM NAD⁺ 0.1 μL;
Phusion® High-Fidelity DNA Polymerase 1 μL;
when the template is RNA,
Nuclease-free water 5.5 μL;
50 ng/μL template RNA 2 μL;
$3 \times 10^{-3}$ μM of the probe 1 μL;
RNase Inhibitor 0.5 μL;
10×Ampligase Buffer 1 μL;

denaturing at 70° C. for 2 min, and incubating at 65° C. for 2 h; then adding the following reagents, reacting at 42° C. for 1 h, and performing extending and ligating reactions;

1 mM dNTPs 1 µL;
5 U/µL Ampligase DNA ligase 1 µL;
10×Ampligase Buffer 1 µL;
50 mM NAD⁺ 0.1 µL;
5×First-Strand Buffer 4 µL;
100 mM DTT 2 µL;
SMART MMLV RT 1 µL.

12. The method of claim 10, wherein when it is adding the template DNA, the probe, and polymerase and ligase simultaneously, and performing hybridizing, extending and ligating simultaneously to obtain the first product, the reaction system and reaction procedure of the hybridizing, extending and ligating reaction are:

Purified water 3.4 µL;
50 ng/µL template DNA 2 µL;
3×10⁻³ µM of the probe 1 µL;
1 mM dNTPs 1 µL;
5 U/µL Ampligase DNA ligase 1 µL;
10×Ampligase Buffer 1 µL;
50 mM NAD⁺ 0.1 µL;
Phusion® HiFi DNA Polymerase 0.5 µL;
The reaction procedure is: at 95° C. for 5 min and at 60° C. for 3 h.

13. The method of claim 9, wherein the obtaining of the second product is: firstly digesting the remaining probe and template DNA using an exonuclease, then linearizing the first product using a USER enzyme, and then performing a PCR amplification through a tag primer, to obtain the second product;

or adding the exonuclease and tag upstream primer, tag downstream primer simultaneously, and performing enzyme digesting, linearizing and PCR amplifying simultaneously to obtain the second product, wherein the tag upstream primer and the tag downstream primer have a phosphorothioate modification at a 3' end and a thio, amino or spacer arm modification at the 5' end to protect the primer from being enzyme digested by the exonuclease.

14. The method of claim 13, wherein when it is firstly digesting the remaining probe and template DNA using an exonuclease, then linearizing the first product using a USER enzyme, and then performing a PCR amplification through a tag primer, to obtain the second product, the reaction system and procedure of obtaining of the second product are:

The first product
Exonuclease I 0.5 µL;
Exonuclease III 0.5 µL;
incubating at 37° C. for 40 min, and incubating at 95° C. for 5 min;

and then adding the following reagents:
2×iProof HF Master Mix 50 µL;
Purified water 29 µL;
20 µM tag upstream primer 2 µL;
20 µM tag downstream primer 2 µL;
USER enzyme 1 µL;
incubating at 37° C. for 15 min, and pre-denaturing at 98° C. for 30 s; denaturing at 98° C. for 10 s, annealing at 58° C. for 30 s, extending at 72° C. for 30 s, and 26 cycles; extending at 72° C. for 2 min, and heat preserving at 4° C.

15. The method of claim 13, wherein when it is adding the exonuclease and tag upstream primer, tag downstream primer simultaneously, and performing enzyme digesting, linearizing and PCR amplifying simultaneously to obtain the second product, when the template is the DNA, the reaction system and procedure of obtaining of the second product are:

The first product 18 µL;
Exonuclease Lambda 0.5 µL;
Exonuclease III 1 µL;
2×iProof HF Master Mix 50 µL;
H₂O 29.5 µL;
20 µM tag upstream primer 2 µL;
20 µM tag downstream primer 2 µL;
the procedure is: incubating at 37° C. for 5 min, incubating at 95° C. for 5 min, and pre-denaturing at 98° C. for 30 s; annealing at 58° C. for 30 s, extending at 72° C. for 30 s, and 26 cycles, extending at 72° C. for 2 min, and heat preserving at 4° C.;

or, when the template is the RNA, the reaction system and procedure are:
The first product 10.1 µL;
Exonuclease I 1 µL;
RNase A 0.1 µL;
RNase H 0.1 µL;
2×iProof HF Master Mix 50 µL;
H₂O 24.8 µL;
20 µM tag upstream primer 2 µL;
20 µM tag downstream primer 2 µL;
incubating at 37° C. for 60 min, incubating at 95° C. for 5 min, and pre-denaturing at 98° C. for 30 s; denaturing at 98° C. for 10 s, annealing at 60° C. for 30 s, extending at 72° C. for 30 s, and 27 cycles; extending at 72° C. for 2 min, and heat preserving at 4° C.

16. The method of claim 13, wherein a structure of the upstream primer of the tag primers, starting from the 5' end, is a sequence region for cluster generation and an index sequence region for Illumina sequencing; and a full-length sequence region inversely complementary paired with an Illumina Tag1 sequence;

and a structure of the downstream primers of the tag primers, starting from the 5' end, is a sequence region for cluster generation and an index sequence region for Illumina sequencing; and an Illumina Tag2 full-length sequence region.

\* \* \* \* \*

SEQUENCE LISTING

```
<160> NUMBER OF SEQ ID NOS: 16

<210> SEQ ID NO 1
<211> LENGTH: 120
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: C phosphorylation of 5' end
<220> FEATURE:
<221> NAME/KEY: misc_feature
<222> LOCATION: (27)..(38)
<223> OTHER INFORMATION: n is a, c, g, or t

<400> SEQUENCE: 1
gggccgcttc attttgtaag acttatnnnn nnnnnnnnct gtctcttata cacatctccg      60
agcccacgag acacactctt tccctacacg acgctcttcc gatcttgtct gctccacttc     120

<210> SEQ ID NO 2
<211> LENGTH: 129
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: C phosphorylation of 5' end
<220> FEATURE:
<221> NAME/KEY: misc_feature
<222> LOCATION: (46)..(47)
<223> OTHER INFORMATION: V=g or a or c
<220> FEATURE:
<221> NAME/KEY: misc_feature
<222> LOCATION: (89)..(100)
<223> OTHER INFORMATION: n is a, c, g, or t

<400> SEQUENCE: 2
ctctttatac tcttaaaaat tactgaggac ctaaaagagc atttgvvctg tctcttatac      60
```

```
acatctccga acgacgctct tccgatctnn nnnnnnnnnn aaatgaattt gacaggataa    120
tagaaaatc                                                            129
```

<210> SEQ ID NO 3
<211> LENGTH: 77
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: T phosphorylation of 5' end
<220> FEATURE:
<221> NAME/KEY: misc_feature
<222> LOCATION: (16)..(59)
<223> OTHER INFORMATION: v=g or a or c; b=g or t or c; d=g or a or t;
    n=a or t or g or c

<400> SEQUENCE: 3

```
tgcattcttc aaagcvbdnn nctgtctctt atacacatcc gctcttccga tctnnnbdbg    60
aggtacctga atcagca                                                   77
```

<210> SEQ ID NO 4
<211> LENGTH: 90
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: C phosphorylation of 5' end
<220> FEATURE:
<221> NAME/KEY: misc_feature
<222> LOCATION: (24)..(72)
<223> OTHER INFORMATION: b=g or t or c;n=a or t or g or c;h=a or t or c

<400> SEQUENCE: 4

```
cagtgtttag aatcaggtca ctcbnnnnnc tgtctcttat acacatctcc gacgctcttc    60
cgatctnnnn nhcccagttt gaagcaaatg                                     90
```

<210> SEQ ID NO 5
<211> LENGTH: 123
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: G phosphorylation of 5' end
<220> FEATURE:
<221> NAME/KEY: misc_feature
<222> LOCATION: (27)..(38)
<223> OTHER INFORMATION: n is a, c, g, or t
<220> FEATURE:
<221> NAME/KEY: misc_feature
<222> LOCATION: (73)..(75)
<223> OTHER INFORMATION: n is deoxyuridine

<400> SEQUENCE: 5

```
gggccgcttc attttgtaag acttatnnnn nnnnnnnct gtctcttata cacatctccg     60
agcccacgag acnnnacact ctttccctac acgacgctct tccgatcttg tctgctccac   120
ttc                                                                  123
```

<210> SEQ ID NO 6

-continued

```
<211> LENGTH: 130
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: C phosphorylation of 5' end
<220> FEATURE:
<221> NAME/KEY: misc_feature
<222> LOCATION: (46)..(47)
<223> OTHER INFORMATION: v=g or a or c
<220> FEATURE:
<221> NAME/KEY: misc_feature
<222> LOCATION: (71)..(71)
<223> OTHER INFORMATION: n is deoxyuridine
<220> FEATURE:
<221> NAME/KEY: misc_feature
<222> LOCATION: (90)..(101)
<223> OTHER INFORMATION: n is a, c, g, or t

<400> SEQUENCE: 6
ctctttatac tcttaaaaat tactgaggac ctaaaagagc atttgvvctg tctcttatac      60
acatctccga nacgacgctc ttccgatctn nnnnnnnnnn naaatgaatt tgacaggata    120
atagaaaatc                                                            130

<210> SEQ ID NO 7
<211> LENGTH: 80
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: T phosphorylation of 5' end
<220> FEATURE:
<221> NAME/KEY: misc_feature
<222> LOCATION: (16)..(21)
<223> OTHER INFORMATION: v=g or a or c ; b=g or t or c;d=g or a or t;n=a
      or t or g or c
<220> FEATURE:
<221> NAME/KEY: misc_feature
<222> LOCATION: (40)..(40)
<223> OTHER INFORMATION: n is deoxyuridine
<220> FEATURE:
<221> NAME/KEY: misc_feature
<222> LOCATION: (57)..(62)
<223> OTHER INFORMATION: n=a or t or g or c; b=g or t or c;d=g or a or t

<400> SEQUENCE: 7
tgcattcttc aaagcvbdnn nctgtctctt atacacatcn gacgctcttc cgatctnnnb      60
dbgaggtacc tgaatcagca                                                  80

<210> SEQ ID NO 8
<211> LENGTH: 93
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: C phosphorylation of 5' end
<220> FEATURE:
<221> NAME/KEY: misc_feature
<222> LOCATION: (24)..(29)
<223> OTHER INFORMATION: b=g or t or c; n=a or t or g or c
<220> FEATURE:
<221> NAME/KEY: misc_feature
<222> LOCATION: (51)..(51)
```

```
<223> OTHER INFORMATION: n is deoxyuridine
<220> FEATURE:
<221> NAME/KEY: misc_feature
<222> LOCATION: (68)..(75)
<223> OTHER INFORMATION: n=a or t or g or c; d=g or a or t; b=g or t or
      c; h=a or t or c

<400> SEQUENCE: 8
cagtgtttag aatcaggtca ctcbnnnnnc tgtctcttat acacatctcc ngacgctctt      60
ccgatctnnn nndbhcccag tttgaagcaa atg                                  93

<210> SEQ ID NO 9
<211> LENGTH: 66
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (65)..(66)
<223> OTHER INFORMATION: Phosphorothioate modification

<400> SEQUENCE: 9
caagcagaag acggcatacg agatttctgc ctgtctcgtg ggctcggaga tgtgtataag      60
agacag                                                                66

<210> SEQ ID NO 10
<211> LENGTH: 70
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (69)..(70)
<223> OTHER INFORMATION: Phosphorothioate modification

<400> SEQUENCE: 10
aatgatacgg cgaccaccga gatctacact atagcctaca ctctttccct acacgacgct      60
cttccgatct                                                            70

<210> SEQ ID NO 11
<211> LENGTH: 66
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(2)
<223> OTHER INFORMATION: Phosphorothioate modification
<220> FEATURE:
<221> NAME/KEY: modified_base
<222> LOCATION: (65)..(66)
<223> OTHER INFORMATION: Phosphorothioate modification

<400> SEQUENCE: 11
caagcagaag acggcatacg agatttctgc ctgtctcgtg ggctcggaga tgtgtataag      60
agacag                                                                66

<210> SEQ ID NO 12
<211> LENGTH: 70
<212> TYPE: DNA
<213> ORGANISM: Artificial Sequence
<220> FEATURE:
<223> OTHER INFORMATION: Synthetic: Designed based on base sequence
<220> FEATURE:
```

```
<221> NAME/KEY: modified_base
<222> LOCATION: (1)..(2)
<223> OTHER INFORMATION: Phosphorothioate modification
<220> FEATURE:
<221> NAME/KEY: modified_base
<222> LOCATION: (69)..(70)
<223> OTHER INFORMATION: Phosphorothioate modification

<400> SEQUENCE: 12
aatgatacgg cgaccaccga gatctacact atagcctaca ctctttccct acacgacgct      60
cttccgatct                                                            70

<210> SEQ ID NO 13
<211> LENGTH: 119
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: A phosphorylation of 5' end
<220> FEATURE:
<221> NAME/KEY: misc_feature
<222> LOCATION: (21)..(28)
<223> OTHER INFORMATION: h=a or t or c; v=g or a or c ; d=g or a or t;
     n=a or t or g or c
<220> FEATURE:
<221> NAME/KEY: misc_feature
<222> LOCATION: (50)..(50)
<223> OTHER INFORMATION: n is deoxyuridine
<220> FEATURE:
<221> NAME/KEY: misc_feature
<222> LOCATION: (67)..(74)
<223> OTHER INFORMATION: n=a or t or g or c; h=a or t or c

<400> SEQUENCE: 13
agctccatct gcatggcttg hvdnnnnnct gtctcttata cacatctccn gacgctcttc      60
cgatctnnnn nhhhaggtgt gggctctaca gtagttttgc tccatataag catgactcc     119

<210> SEQ ID NO 14
<211> LENGTH: 97
<212> TYPE: DNA
<213> ORGANISM: Artificial Sequence
<220> FEATURE:
<223> OTHER INFORMATION: Synthetic: Designed based on base sequence
<220> FEATURE:
<221> NAME/KEY: modified_base
<222> LOCATION: (1)..(1)
<223> OTHER INFORMATION: A phosphorylation of 5' end
<220> FEATURE:
<221> NAME/KEY: misc_feature
<222> LOCATION: (21)..(28)
<223> OTHER INFORMATION: h=a or t or c; v=g or a or c ; d=g or a or t;
     n=a or t or g or c
<220> FEATURE:
<221> NAME/KEY: misc_feature
<222> LOCATION: (50)..(50)
<223> OTHER INFORMATION: n is deoxyuridine
<220> FEATURE:
<221> NAME/KEY: misc_feature
<222> LOCATION: (67)..(74)
<223> OTHER INFORMATION: n=a or t or g or c;b=g or t or c

<400> SEQUENCE: 14
agctccatct gcatggcttg hvdnnnnnct gtctcttata cacatctccn gacgctcttc      60
cgatctnnnn nbbbcgcgag ttgacatttt tgcttgg                              97

<210> SEQ ID NO 15
<211> LENGTH: 34
```

```
<212> TYPE: DNA
<213> ORGANISM: Artificial Sequence
<220> FEATURE:
<223> OTHER INFORMATION: Synthetic: Designed based on base sequence

<400> SEQUENCE: 15
ctgtctctta tacacatctc cgagcccacg agac                    34

<210> SEQ ID NO 16
<211> LENGTH: 33
<212> TYPE: DNA
<213> ORGANISM: Artificial Sequence
<220> FEATURE:
<223> OTHER INFORMATION: Synthetic: Designed based on base sequence

<400> SEQUENCE: 16
acactctttc cctacacgac gctcttccga tct                     33
```